United States Patent
Cadieux et al.

(10) Patent No.: US 10,362,806 B2
(45) Date of Patent: **\*Jul. 30, 2019**

(54) ELECTRONIC VAPING DEVICE AND COMPONENTS THEREOF

(71) Applicant: Altria Client Services LLC, Richmond, VA (US)

(72) Inventors: Edmond J. Cadieux, Mechanicsville, VA (US); Douglas A. Burton, Glen Allen, VA (US); Barry S. Smith, Hopewell, VA (US); Peter Lipowicz, Midlothian, VA (US); Patrick J. Cobler, Andover, MA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/860,938

(22) Filed: Jan. 3, 2018

(65) Prior Publication Data

US 2018/0125119 A1    May 10, 2018

Related U.S. Application Data

(62) Division of application No. 14/634,124, filed on Feb. 27, 2015, now Pat. No. 9,888,719.

(Continued)

(51) Int. Cl.
  *A61M 15/06* (2006.01)
  *A24F 47/00* (2006.01)
(52) U.S. Cl.
  CPC .......... *A24F 47/008* (2013.01); *A61M 15/06* (2013.01)

(58) Field of Classification Search
  CPC .................................................. A24F 47/008
  See application file for complete search history.

(56) References Cited

U.S. PATENT DOCUMENTS

| 5,613,505 A | 3/1997 | Campbell et al. |
| 5,649,554 A | 7/1997 | Sprinkel et al. |

(Continued)

FOREIGN PATENT DOCUMENTS

| CN | 1126426 A | 7/1996 |
| CN | 201445686 U | 5/2010 |

(Continued)

OTHER PUBLICATIONS

International Search Report and Written Opinion dated Jun. 8, 2015.

(Continued)

*Primary Examiner* — Anthony Calandra
(74) *Attorney, Agent, or Firm* — Harness, Dickey & Pierce, P.L.C.

(57) ABSTRACT

A liquid reservoir component of an electronic vaping device includes an outer casing extending in a longitudinal direction, an air inlet, and a vapor outlet. An inner tube is within the outer casing defining a central air passage communicates with the inlet and the outlet. A liquid reservoir is in an annular space between the outer casing and the inner tube. A susceptor is adjacent the central air passage, and a wick is in communication with the liquid reservoir and in thermal communication with the susceptor such that the susceptor is operable to heat the liquid material to a temperature to vaporize the liquid material and form a vapor in the central air passage. The liquid reservoir component is configured to connect with a power supply component such that an induction source is operable to generate an inductive field to heat the susceptor when powered by the power source.

19 Claims, 14 Drawing Sheets

Related U.S. Application Data

(60) Provisional application No. 61/946,376, filed on Feb. 28, 2014.

(56) References Cited

U.S. PATENT DOCUMENTS

| | | |
|---|---|---|
| 2012/0234315 A1 | 9/2012 | Li et al. |
| 2012/0279512 A1 | 11/2012 | Hon |
| 2013/0192615 A1 | 8/2013 | Tucker et al. |
| 2013/0213419 A1 | 8/2013 | Tucker et al. |
| 2013/0220315 A1 | 8/2013 | Conley et al. |
| 2013/0276804 A1 | 10/2013 | Hon |
| 2014/0353856 A1 | 12/2014 | Dubief |
| 2017/0055585 A1 | 3/2017 | Fursa et al. |

FOREIGN PATENT DOCUMENTS

| | | |
|---|---|---|
| CN | 203327950 U | 12/2013 |
| EP | 2327318 A1 | 6/2011 |
| WO | WO-2013/060743 A2 | 5/2013 |
| WO | WO-2013083636 A1 | 6/2013 |
| WO | WO-2013/155645 A1 | 10/2013 |
| WO | WO-2014/023967 A1 | 2/2014 |

OTHER PUBLICATIONS

Singapore Search Report and Written Opinion dated Oct. 2, 2017.
Philippines Substantive Examination Report dated Sep. 18, 2018.
"Accelerated and advanced training courses for heat treatment workers," China Machine Press, First Edition, Apr. 2008, pp. 104-106.
Chinese Office Action and English translation thereof dated Jul. 18, 2018.
Official Notification issued by the Eurasian Patent Office on Jun. 28, 2018 for Eurasian Patent Application No. 201691744 (PCT/US2015/018035) (and English translation).
Chinese Office Action and English translation thereof dated Feb. 11, 2019.

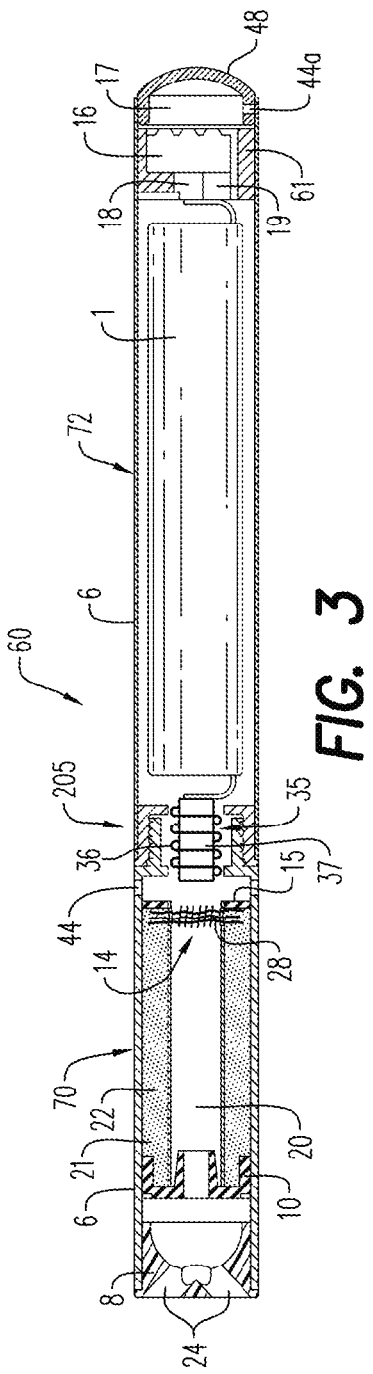
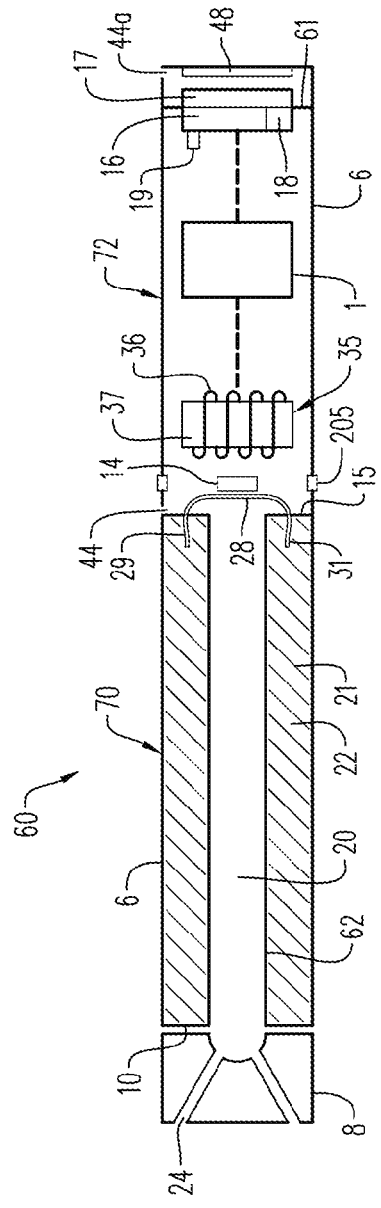

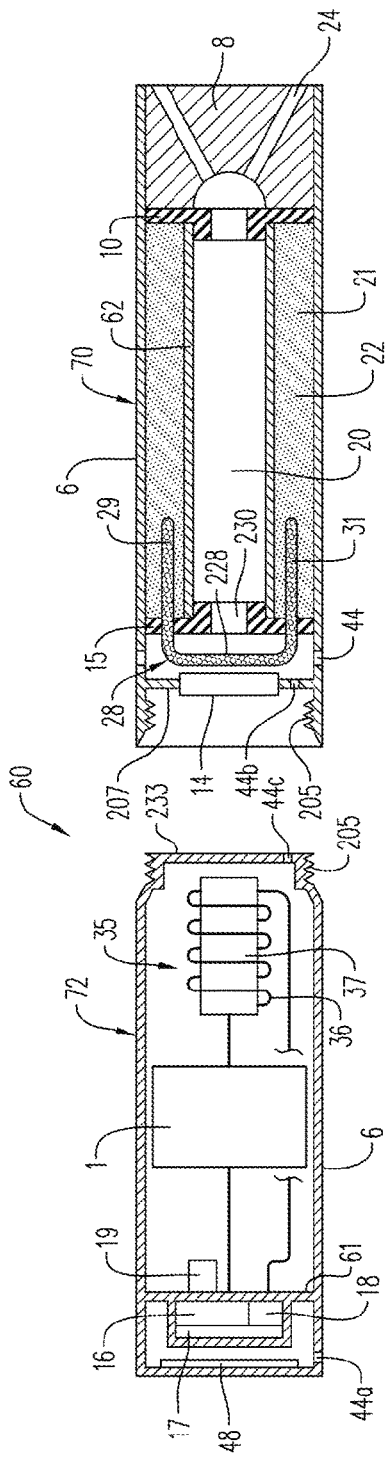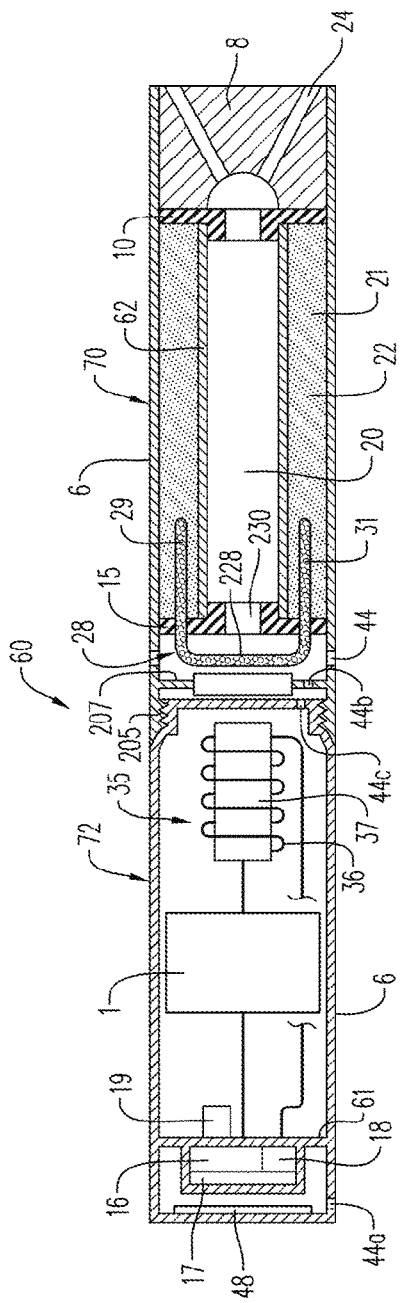

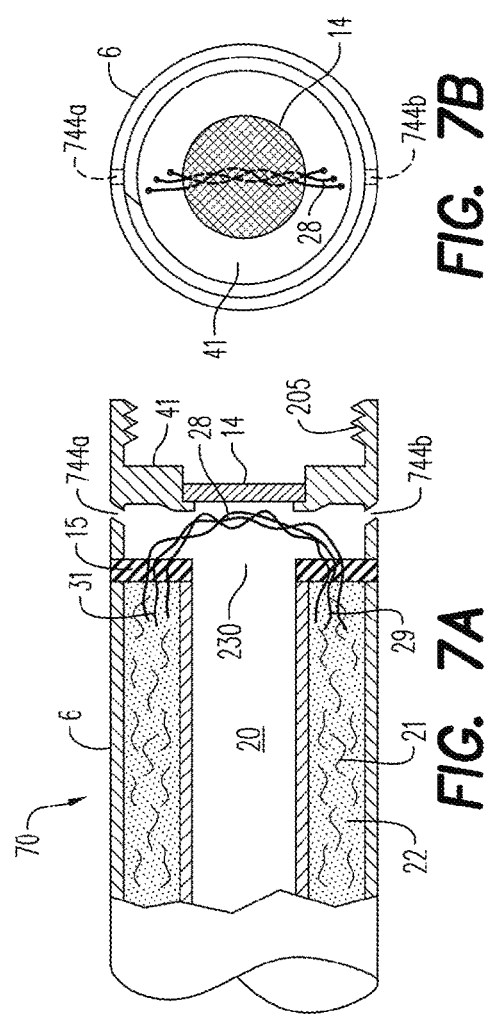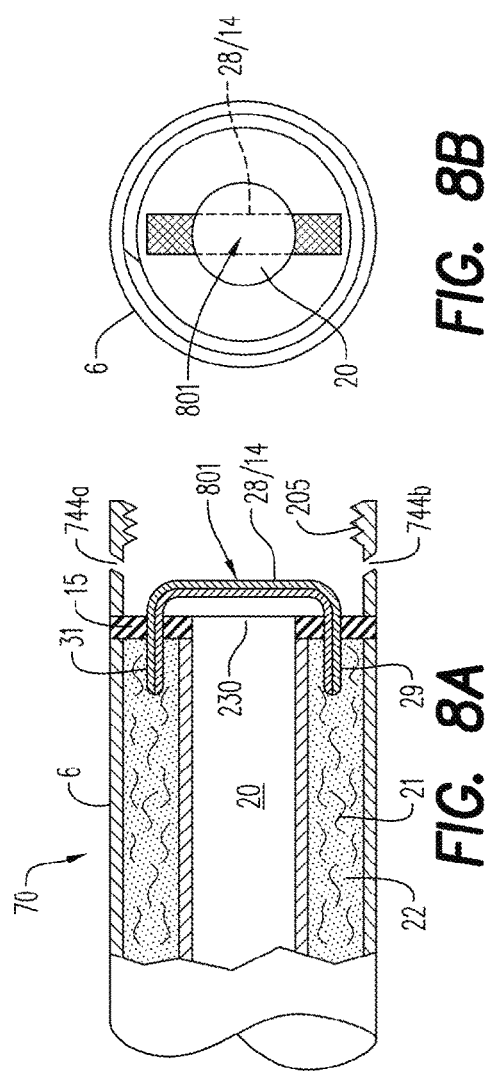

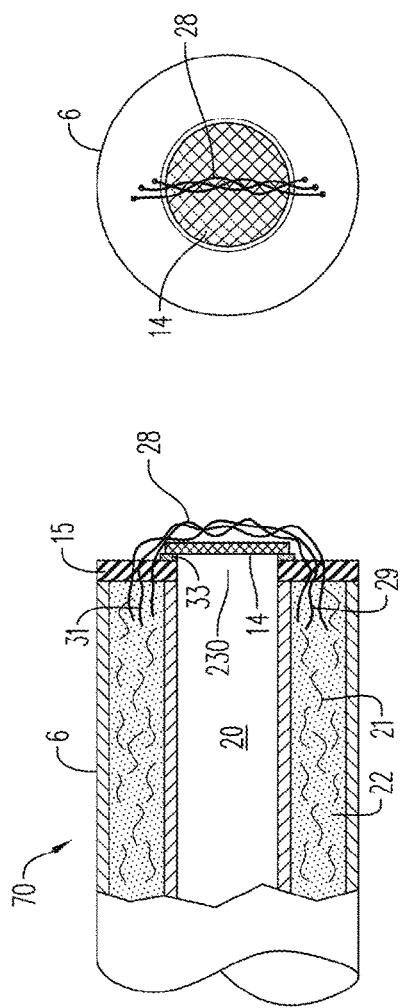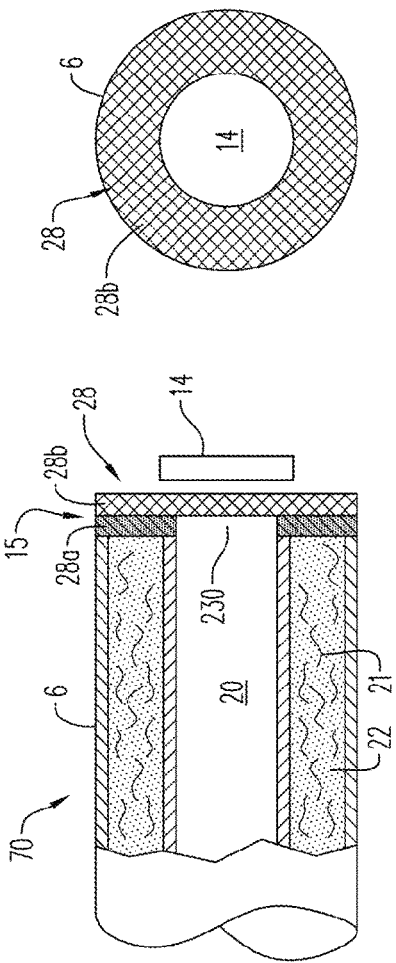

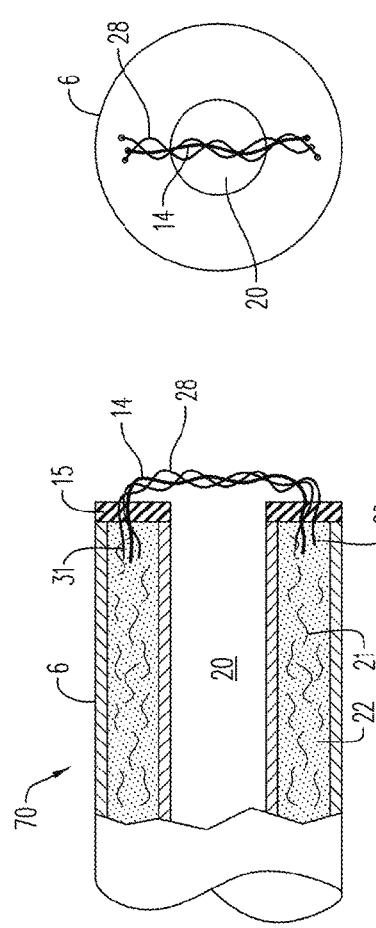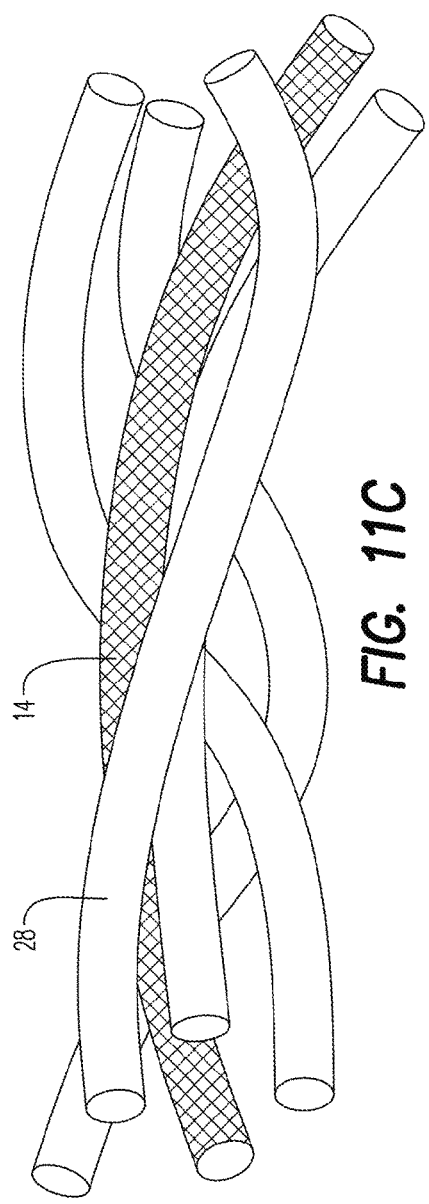

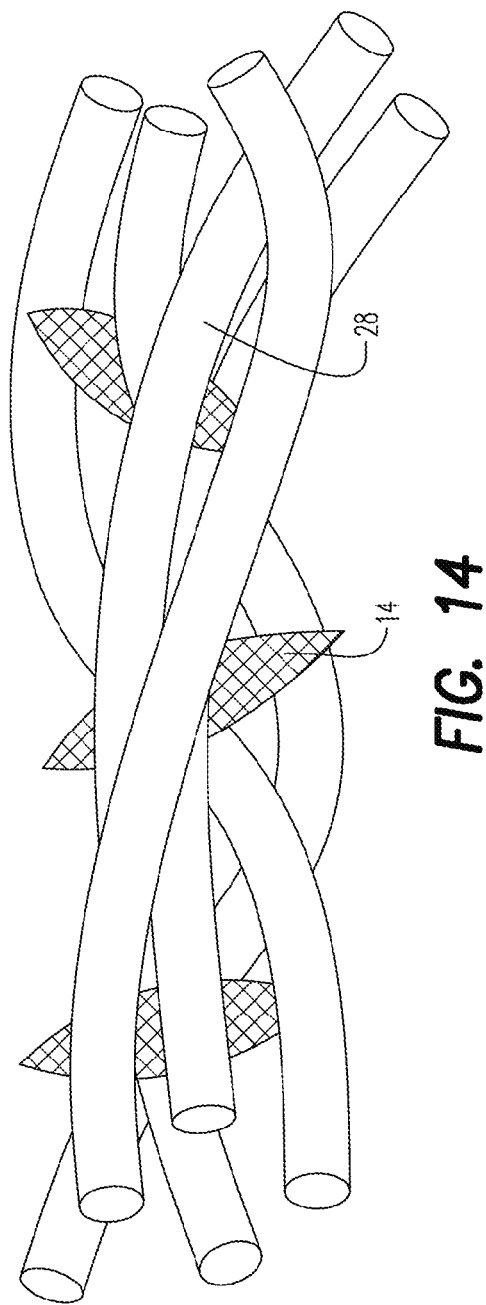

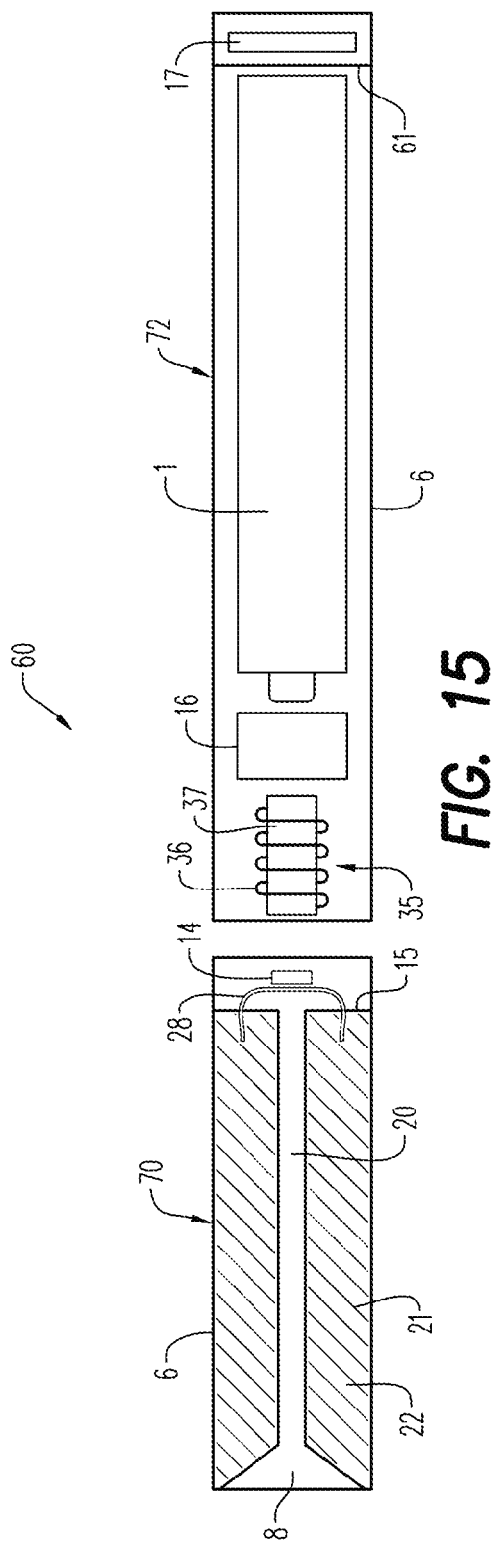

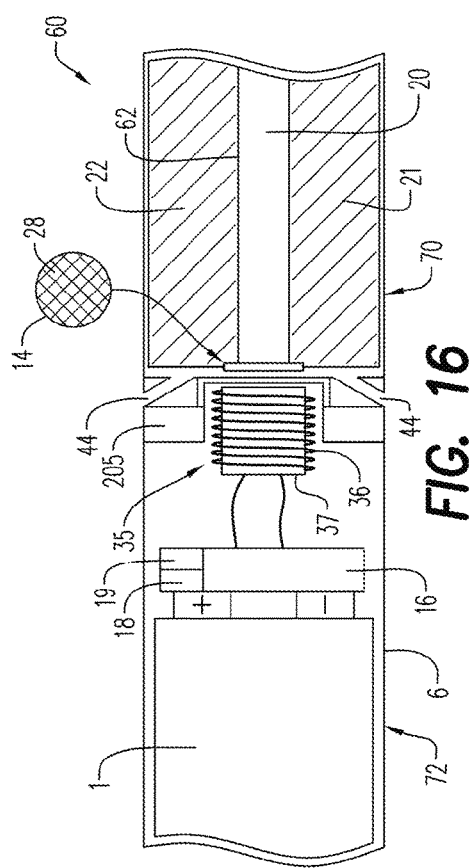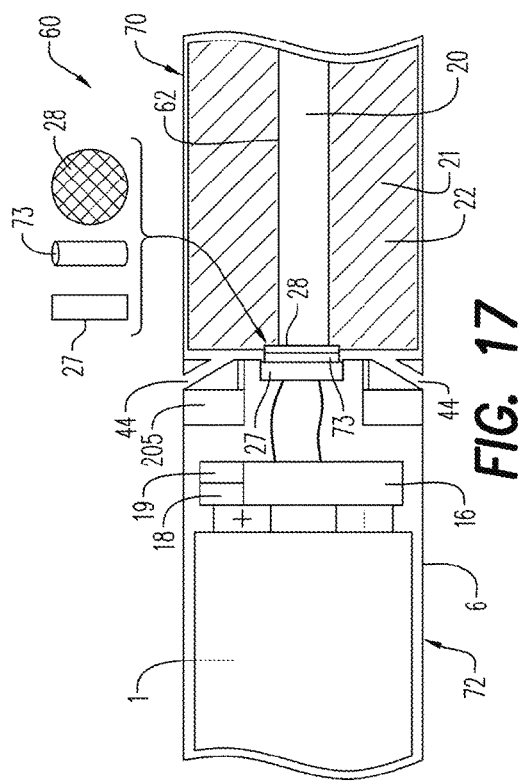

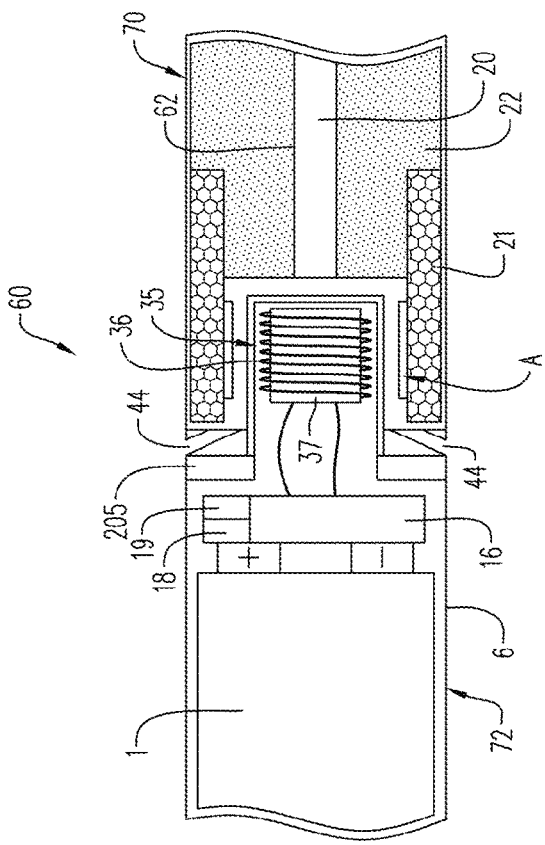
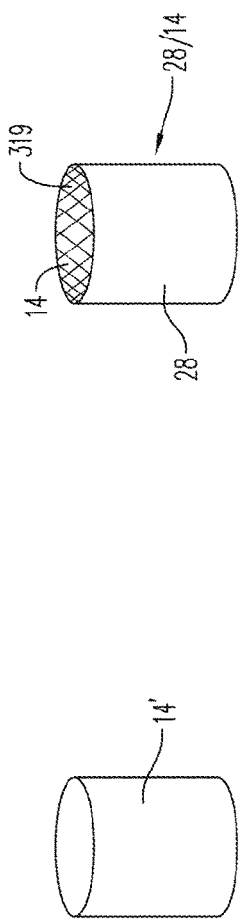

ELECTRONIC VAPING DEVICE AND COMPONENTS THEREOF

CROSS-REFERENCE TO RELATED APPLICATIONS

This application is a divisional application of and claims priority under 35 U.S.C. §§ 120,121 to U.S. application Ser. No. 14/634,124 filed Feb. 27, 2015, which claims the benefit of provisional U.S. Application No. 61/946,376 filed on Feb. 28, 2014, the entire contents of each of which are hereby incorporated herein by reference.

BACKGROUND

1. Field

Example embodiments relate generally to an e-vaping device.

2. Related Art

Electronic vaping (e-vaping) devices are used to vaporize a liquid material into a vapor in order for an adult vaper to inhale the vapor. These electronic vaping devices may be referred to as e-vaping devices. E-vaping devices include a heater which vaporizes liquid material to produce a vapor. An e-vaping device may include several e-vaping elements including a power source, a cartridge or e-vaping tank including the heater and along with a reservoir capable of holding the liquid material. During the usage of these devices, once the liquid in the cartridge is exhausted, an adult vaper may replace it with a new cartridge containing fresh liquid, for continuing the usage of the device.

SUMMARY

At least one example embodiment discloses a liquid reservoir liquid reservoir component of an electronic vaping (e-vaping) device including an outer casing extending in a longitudinal direction, an air inlet, a vapor outlet, an inner tube within the outer casing defining a central air passage communicating with the air inlet and the vapor outlet, a liquid reservoir configured to contain a liquid material, the liquid reservoir in an annular space between the outer casing and the inner tube, a susceptor located adjacent the central air passage and a wick extending across the central air passage in communication with the liquid reservoir and configured to be in thermal communication with the susceptor such that the susceptor is operable to heat the liquid material to a temperature to vaporize the liquid material and form a vapor in the central air passage. The liquid reservoir component is configured to connect with a power supply component, the power supply component containing a power source in electrical communication with an induction source, the induction source being axially spaced from the susceptor by a distance if the liquid reservoir component is attached to the power supply component such that the induction source is operable to generate an inductive field to heat the susceptor if powered by the power source.

In an example embodiment, the susceptor is wound about the wick, and the susceptor is a coil heater.

In an example embodiment, the susceptor is wound about the wick, the susceptor is a ribbon of mesh material, and the mesh material is at least one of electrically resistive and electrically conductive.

In an example embodiment, the susceptor is integrated with the wick, and the susceptor is at least one conductive filament.

In an example embodiment, the susceptor is integrated with the wick, and the susceptor is a conductive rod extending through filaments of the wick.

In an example embodiment, the susceptor is integrated with the wick, the susceptor is conductive flakes, and the conductive flakes are in the wick.

In an example embodiment, the susceptor is integrated with the wick and the susceptor is a portion of a conductive mesh in the inductive field.

In an example embodiment, the susceptor is a conductive plate in contact with a portion of the wick.

In an example embodiment, the susceptor is a conductive mesh in contact with a portion of the wick.

In an example embodiment, the susceptor comprises at least one material selected of stainless steel, copper, copper alloys, ceramic material coated with film resistive material, nickel chromium alloys, and combinations thereof.

In an example embodiment, the susceptor is made of a magnetic material.

In an example embodiment, the wick is formed from a plurality of filaments.

In an example embodiment, the wick is formed from a porous foam.

In an example embodiment, the wick is made of glass, fiberglass, ceramic, metal, graphite, or polymer material.

In an example embodiment, the liquid reservoir comprises gauze sealed at an upstream end and at a downstream end with a seal.

In an example embodiment, the e-vaping device has a uniform diameter of less than about 10 mm.

At least one example embodiment discloses an electronic vaping (e-vaping) device including a liquid reservoir component connectable to a power supply component. The liquid reservoir component includes an outer casing extending in a longitudinal direction, an air inlet, a vapor outlet, an inner tube within the outer casing defining a central air passage communicating with the air inlet and the vapor outlet, a liquid reservoir configured to contain a liquid material, the liquid reservoir being in an annular space between the outer casing and the inner tube, a susceptor located adjacent the central air passage, and a wick in communication with the liquid reservoir and configured to be in thermal communication with the susceptor such that the susceptor is operable to heat the liquid material to a temperature to vaporize the liquid material. The power supply component includes an outer casing extending in a longitudinal direction including a power source in electrical communication with an induction source, the induction source being axially spaced from the susceptor by a distance if the power supply component is attached to the liquid reservoir component such that the induction source is operable to generate an inductive field to heat the susceptor if powered by the power source such that the susceptor heats the liquid material to a temperature to vaporize the liquid material.

In an example embodiment, the induction source includes an inductive coil at an end thereof proximate to the susceptor of the liquid reservoir component, and the inductive coil is configured to generate the inductive field to heat the susceptor.

In an example embodiment, the inductive coil comprises a helix extending in the longitudinal direction of the outer casing.

In an example embodiment, the inductive coil comprises a planar coil.

In an example embodiment, the inductive coil comprises a helix extending in a transverse direction to the longitudinal direction of the outer casing.

In an example embodiment, the induction source further includes a cylindrical core comprising a ferrite material, the inductive coil is wound about the core and the core extends in one of the longitudinal direction of the outer casing and in a transverse direction to the longitudinal direction of the outer casing.

In an example embodiment, the susceptor is wound about the wick, and the susceptor is a coil heater.

In an example embodiment, the susceptor is wound about the wick, the susceptor is a ribbon of mesh material, and the mesh material is at least one of electrically resistive and electrically conductive.

In an example embodiment, the susceptor is integrated with the wick, and the susceptor is at least one conductive filament.

In an example embodiment, the susceptor is integrated with the wick, and the susceptor is a conductive rod extending through filaments of the wick.

In an example embodiment, the susceptor is integrated with the wick, the susceptor is conductive flakes, and the conductive flakes are in the wick.

In an example embodiment, the susceptor is integrated with the wick and the susceptor is a portion of a conductive mesh in the inductive field.

In an example embodiment, the susceptor is a conductive plate in contact with a portion of the wick.

In an example embodiment, the susceptor is a conductive mesh in contact with a portion of the wick.

In an example embodiment, the susceptor comprises at least one of stainless steel, copper, copper alloys, ceramic material coated with film resistive material, nickel chromium alloys, and combinations thereof.

In an example embodiment, the liquid reservoir component further includes a mouth end insert and the mouth end insert is in communication with the air inlet.

In an example embodiment, the susceptor is axially spaced from a proximate end of the induction source by about 0.01 to 2 mm if the liquid reservoir component is connected to the power supply component.

In an example embodiment, a portion of the power supply component is in the liquid reservoir component if the power supply component and the liquid reservoir component are connected and the susceptor is axially spaced from the proximate end of the induction source or a portion of the liquid reservoir component is in the power supply component if the power supply component and the liquid reservoir component are connected and the susceptor is axially spaced from a proximate end of the induction source.

In an example embodiment, the power supply component further comprises control circuitry including a puff sensor, and the puff sensor is configured to sense air flow and initiate generation of the inductive field from the induction source in electrical communication with the power source.

In an example embodiment, the puff sensor is configured to generate more than one signal responsive to the magnitude of a puff or draw upon the e-vaping device such that the control circuitry can discriminate between the signals to adjust the frequency, magnitude, and/or length of time of the power cycle in response to the signal the control circuitry receives from the puff sensor.

In an example embodiment, the control circuitry is configured to control a variable power cycle from the power source to the induction source as a function of an output signal of the puff sensor.

In an example embodiment, at least one of the liquid reservoir component is connected to the power supply component with a mechanical or magnetic connection, and the liquid reservoir component is a disposable downstream section and the power supply component is a reusable upstream section.

In an example embodiment, the susceptor is made of a magnetic material.

In an example embodiment, the wick is formed from a plurality of filaments.

In an example embodiment, the wick is formed from a porous foam.

In an example embodiment, the wick is made of glass, fiberglass, ceramic, metal, graphite, or polymer material.

In an example embodiment, an electronic article comprising the e-vaping has a uniform diameter of about 10 mm or less, wherein the power supply component further includes a puff sensor configured to sense air flow and initiate generation of the inductive field from the induction source in electrical communication with the power source, and a light-emitting diode (LED) at a free end of the power supply component and the LED is configured to light up when if inductive field is generated.

At least one example embodiment discloses a liquid reservoir component of an electronic vaping (e-vaping) device including an outer casing extending in a longitudinal direction, an air inlet, a vapor outlet, the vapor outlet and air inlet at least partially defining two air passages, a liquid reservoir configured to contain a liquid material, the liquid reservoir in the outer casing, the at least two air passages extending along an outer periphery of the liquid reservoir, a respective susceptor located adjacent to each air passage and a respective wick in communication with the liquid reservoir and configured to be in thermal communication with each respective susceptor such that each wick delivers liquid material to the respective susceptor wherein each susceptor is configured to heat the liquid material to a temperature to vaporize the liquid material. The liquid reservoir component is configured to connect with a power supply component, the power supply component containing a power source in electrical communication with an induction source, the induction source being axially spaced from each respective susceptor if the liquid reservoir component is attached to the power supply component such that the induction source is configured to generate an inductive field to heat each respective susceptor if powered by the power source.

In an example embodiment, an electronic vaping (e-vaping) device includes the liquid reservoir component and has a uniform diameter of less than about 10 mm.

At least one example embodiment discloses an electronic vaping (e-vaping) device including a liquid reservoir component, the liquid reservoir component including an outer casing extending in a longitudinal direction, an air inlet, a vapor outlet, an inner tube within the outer casing defining a central air passage communicating with the air inlet and the vapor outlet, a liquid reservoir configured to contain a liquid material, the liquid reservoir being in an annular space between the outer casing and the inner tube, and a susceptor located adjacent the central air passage, and a power supply component connectable to the liquid reservoir component, the power supply component including a piezoelectric element including a delivery tube, the delivery tube being configured to enter the liquid reservoir if the power supply component is attached to the liquid reservoir component such that the delivery tube can deliver liquid to the piezoelectric element, the piezoelectric element being configured to deliver liquid droplets to the susceptor such that the susceptor heats the liquid droplets to a temperature to vaporize the liquid droplets, and an outer casing extending in a longitudinal direction, the outer casing including a power source in electrical communication with an induction source, the induction source being axially spaced from the susceptor if the power supply component is attached to the liquid reservoir component such that the induction source is configured to generate an inductive field to heat the susceptor such that the susceptor heats liquid droplets to the temperature to vaporize the liquid droplets.

In an example embodiment, the piezoelectric element is configured to deliver the liquid droplets to the susceptor transversely onto an operative surface of the susceptor, and the operative surface of the susceptor is at an angle relative to the longitudinal axis of the e-vaping device.

In an example embodiment, the piezoelectric element and an operative surface of the susceptor are at an angle relative to the longitudinal axis of the e-vaping device and the piezoelectric element is configured to deliver the liquid droplets to the operative surface of the susceptor transversely onto the operative surface.

In an example embodiment, the e-vaping device has a uniform diameter of less than about 10 mm.

At least one example embodiment discloses an electronic vaping (e-vaping) device including a liquid reservoir component, the liquid reservoir component including, an outer casing extending in a longitudinal direction, an air inlet, a vapor outlet, an inner tube within the outer casing defining a central air passage communicating with the air inlet and the vapor outlet, a liquid reservoir configured to contain a liquid material, the liquid reservoir being in an annular space between the outer casing and the inner tube and a susceptor located adjacent the central air passage and in contact with a liquid supply medium, the liquid supply medium configured to deliver the liquid material from the liquid reservoir to the susceptor such that the susceptor heats the liquid material to a temperature to vaporize the liquid material, and a portion of the liquid storage medium surrounds the susceptor, and a power supply component connectable to the liquid reservoir component, the power supply component including an outer casing extending in a longitudinal direction including a power source in electrical communication with an induction source, the induction source extending into the liquid reservoir component and being surrounded by the susceptor if the power supply component is attached to the liquid reservoir component such that the induction source is operable to generate an inductive field to heat the susceptor if powered by the power source such that the susceptor heats the liquid material to the temperature to vaporize the liquid material.

In an example embodiment, the susceptor is formed of a wicking material configured to wick liquid from the portion of the liquid supply medium towards the central air passage.

In an example embodiment, the induction source includes an inductive coil wound about a cylindrical core, the cylindrical core including a ferrite material and the inductive coil and the cylindrical core extend in the longitudinal direction of the outer casing.

In an example embodiment, the e-vaping device has a uniform diameter of less than about 10 mm.

At least one example embodiment discloses a method of producing a vapor from an electronic vaping (e-vaping) device. The method includes wicking a portion of a liquid material from a liquid reservoir to a location adjacent an inlet portion of an air passageway which is in proximity to a susceptor, the susceptor being in proximity to an induction source, generating a signal indicative of a puff by communicating a draw upon the e-vaping device to a puff sensor, vaporizing at least some of the wicked portion of the liquid material by applying an oscillating power cycle to the induction source responsively to the generated signal so as to heat the susceptor to volatilize at least some of the wicked portion of the liquid material and drawing the volatilized material through the air passageway and the e-vaping device.

In an example embodiment, the drawing draws the volatilized material along a straight air passageway.

In an example embodiment, an electronic vaping (e-vaping) device includes a wick which is in communication with a liquid reservoir wherein the wick is adjacent an inlet portion of an air passageway upstream of a susceptor which is positioned in proximity to an induction source upstream of the wick, wherein the e-vaping device is operable to perform the method.

In an example embodiment, a wick which is in communication with a liquid reservoir wherein the wick is adjacent an inlet portion of an air passageway upstream of a susceptor which is positioned in proximity to an induction source upstream of the wick, wherein the e-vaping device is operable to perform the method.

At least one example embodiment discloses a liquid reservoir component of an electronic vaping (e-vaping) device including an air inlet, an outlet located downstream of the air inlet, a straight internal passageway having an inlet end portion, the straight internal passageway communicating the air inlet and the air outlet through the inlet end portion, a liquid reservoir, a wick including a heatable wick portion and a second wick portion, the heatable wick portion being in proximity of and across at least a portion of the inlet end portion of the straight internal passageway, the second wick portion being arranged to draw liquid from the liquid reservoir to the heatable wick portion and a susceptor in proximal relation to the heatable wick portion, the susceptor configured to produce heat in the presence of an activating, oscillating electromagnetic field to volatilize liquid off the heatable wick portion, the proximity of the heated wick portion to the inlet end portion of the straight internal passageway permits the volatilized liquid to be drawn directly into the inlet end portion of the straight internal passageway.

In an example embodiment, the liquid reservoir component further includes an outer casing having an outlet end portion and an opposite end portion, a connector at the opposite end portion, the connector configured to releasably couple the liquid reservoir component with the separate electromagnetic energy source upon closure and a support arranged to maintain the susceptor in a fixed relation to the opposite end portion of the outer casing such that upon the closure of the connector, the susceptor is axially spaced from the separate electromagnetic energy source by a distance.

In an example embodiment, the wick is a filamentary wick and the susceptor is wound about the heatable wick portion, and the susceptor is a coil heater.

In an example embodiment, the wick is a filamentary wick, the susceptor is wound about the heatable wick portion, and the susceptor is a ribbon of electrically resistive/conductive mesh material.

In an example embodiment, the wick is a filamentary wick, the susceptor is integrated with the wick, and the susceptor is at least one conductive filament intertwined with filaments of the filamentary wick.

In an example embodiment, the wick is a filamentary wick, the susceptor is integrated with the wick, and the susceptor is a conductive rod extending through filaments of the wick.

In an example embodiment, the susceptor is integrated with the wick, the susceptor is conductive flakes and the conductive flakes are in the wick.

In an example embodiment, the susceptor and the wick are integrated into a single wick/susceptor element.

In an example embodiment, the susceptor and the wick have disk-like shapes, and the susceptor is in a superposing relation to the wick and the inlet end portion of the straight internal passageway.

In an example embodiment, the susceptor is a conductive mesh in contact to a portion of the wick.

In an example embodiment, the wick is formed from a plurality of filaments.

In an example embodiment, the wick is formed from a porous foam.

In an example embodiment, the wick is made of glass, fiberglass, ceramic, metal, graphite, or polymer material.

In an example embodiment, the susceptor is formed in a disk-like shape.

BRIEF DESCRIPTION OF THE DRAWINGS

FIG. 3 is a cross-sectional view of an e-vaping device according to an example embodiment disclosed herein.

FIG. 4 is a cross-sectional view of an e-vaping device according to an example embodiment disclosed herein.

FIG. 5 is a cross-sectional view of an e-vaping device according to an example embodiment disclosed herein, with the sections thereof unconnected.

FIG. 6 is a cross-sectional view of the e-vaping device of FIG. 5 with the sections thereof connected.

FIG. 7A is a partial cross-sectional view of a liquid reservoir component of an e-vaping device according to an example embodiment disclosed herein.

FIG. 7B is an end view of the liquid reservoir component of FIG. 7A.

FIG. 8A is a partial, cross-sectional view of a liquid reservoir component of an e-vaping device according to another example embodiment disclosed herein.

FIG. 8B is an end view of the liquid reservoir component of FIG. 8A.

FIG. 9A is a partial, cross-sectional view of a liquid reservoir component of an e-vaping device according to still another example embodiment disclosed herein.

FIG. 9B is an end view of the liquid reservoir component of FIG. 9A.

FIG. 10A is a partial, cross-sectional view of a liquid reservoir component of an e-vaping device according to yet another example embodiment disclosed herein.

FIG. 10B is an end view of the liquid reservoir component of FIG. 10A.

FIG. 11A is a partial, cross-sectional view of a liquid reservoir component of another example embodiment of an e-vaping device comprising an integrated susceptor and wick element.

FIG. 11B is an end view of the liquid reservoir component of FIG. 11A.

FIG. 11C is a detail view of the integrated susceptor and wick element of the example embodiment shown in FIGS. 11A and 11B.

FIG. 14 is a detail view of another example embodiment of an integrated susceptor and wick element, operable in a liquid reservoir component such as shown in FIGS. 11A and 11B.

FIG. 15 is a cross-sectional view of an e-vaping device according to another example embodiment disclosed herein.

FIG. 16 is a cross-sectional view of an e-vaping device according to yet another example embodiment disclosed herein.

FIG. 17 is a cross-sectional view of an e-vaping device according to an example embodiment disclosed herein.

FIG. 18A is a cross-sectional view of an e-vaping device according to an example embodiment disclosed herein.

FIG. 18B is a perspective view of a susceptor formed of an electrically conductive/resistive element that has the capacity to wick liquid material from the liquid reservoir.

FIG. 18C is a perspective view of a susceptor that is coupled with a wicking layer so as to form an integrated wick/susceptor.

DETAILED DESCRIPTION

Figure 1:
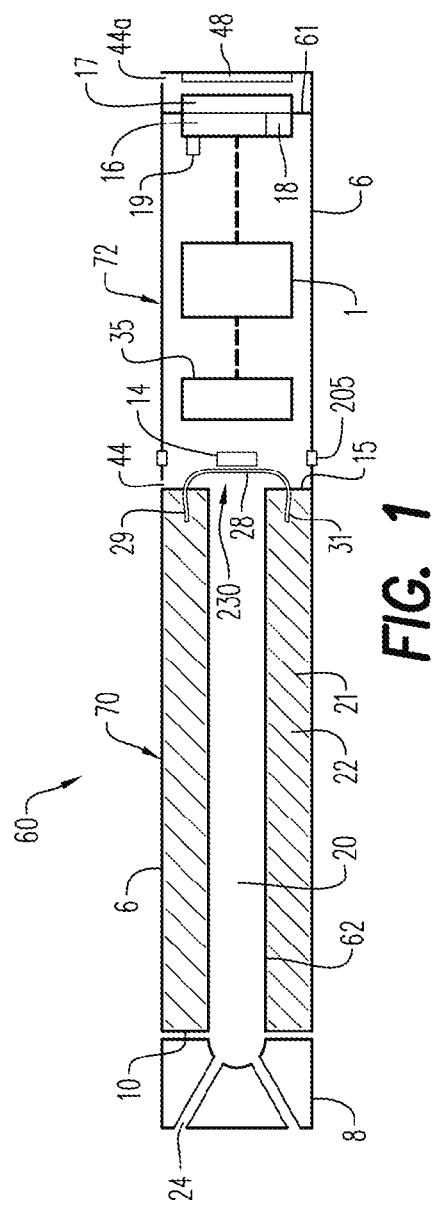
FIG. 1 is a cross-sectional view of an electronic vaping (e-vaping) device according to an example embodiment disclosed herein.

Some detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to"

another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Disclosed herein are novel example embodiments of an electronic vaping (e-vaping) device 60. Referring to FIG. 1, the e-vaping device 60 comprises a liquid reservoir component (first or cartridge section) 70 and a reusable power supply component (battery section) 72, wherein an induction source 35 and a susceptor 14 cooperate to heat and vaporize (volatilize) liquid from a wick 28, which draws liquid from a liquid reservoir 22 of the liquid reservoir component 70. The liquid reservoir component 70 is connectable to the power supply component 72 at a connector 205, such as a threaded connection or by another convenience such as a snug-fit, detent, clamp, clasp and/or magnetic connection. The connector 205 may be a single molded piece to achieve precise placement of the liquid reservoir component 70 and the power supply component 72. Upon closure of the connector 205, the induction source 35 is axially spaced from the susceptor 14 by a predetermined and/or desired amount such that the induction source 35 is operable to generate an oscillating inductive, electromagnetic field that superposes the susceptor 14 and causes the susceptor 14 to heat. The induction source 35 may be axially spaced from the susceptor 14 by less than about 2 mm and more preferably by less than about 1 mm.

The Cartridge Section

Still referring to FIG. 1, the liquid reservoir component or cartridge section 70 may include an outer casing 6 (such as a cylindrical tube) which extends longitudinally and includes air inlet 44. An inner tube 62 disposed within the outer casing 6 defines a straight, central air passage 20 which communicates with the air inlet 44 and a vapor outlet (mouth end insert outlet) 24. There may be two air inlets 44 which communicate with the central air passage 20. Alternatively, there may be three, four, five or more air inlets 44. If there are more than two air inlets, the air inlets 44 are may be located at different locations along the length and/or around the circumference of the e-vaping device 60. Further, altering the size and number of air inlets 44 can also aid in establishing a desired resistance to draw of the e-vaping device 60, reduce generation of a whistling noise during a draw on the e-vaping device 60, and reduce Helmholtz resonance in the central air passage 20.

The liquid reservoir 22 may be established in an annular space between the outer casing 6 and the inner tube 62, wherein the annular space is sealed at an upstream end by an upstream seal 15 and at a downstream location by a downstream seal (or stopper) 10. The liquid reservoir 22 contains a liquid material, and optionally, a liquid storage medium 21 (i.e. fibrous medium) operable to disperse the liquid material in the liquid reservoir 22. For example, the liquid storage medium 21 can be a wrapping of gauze about the inner tube 62. The liquid storage medium 21 may include an outer wrapping of gauze surrounding an inner wrapping of gauze of the same or different material. In one example embodiment, the liquid storage medium 21 of the liquid reservoir 22 is constructed from an alumina ceramic in the form of loose particles, loose fibers, or woven or nonwoven fibers, or alternatively the liquid storage medium 21 is constructed from a cellulosic material such as cotton or gauze material or polymer material, such as polyethylene terephthalate, which may be in the form of a woven fabric or alternatively the polymer material can be in the form of a bundle of loose fibers.

The liquid storage medium 21 may comprise a fibrous material comprising cotton, polyethylene, polyester, rayon and combinations thereof. The fibers may have a diameter ranging in size from about 6 microns to about 15 microns (e.g., about 8 microns to about 12 microns or about 9 microns to about 11 microns). The liquid storage medium 21 can be a sintered, porous, or foamed material. The fibers may be sized to be irrespirable and can have a cross-section which has a y-shape, cross shape, clover shape or any other suitable shape. In the alternative, the liquid reservoir 22 may comprise a liquid filled tank lacking a liquid storage medium 21.

Still referring to FIG. 1, the liquid reservoir component 70 further comprises the susceptor 14 which may be located adjacent an upstream portion of the central air passage 20, and the wick 28 in liquid communication with liquid material in the liquid reservoir 22 and in thermal communication with the susceptor 14. The wick 28 is operable to draw liquid material from the liquid reservoir 22 into a proximate relation with the susceptor 14 such that the susceptor 14, upon activation by the induction source 35, heats the liquid material to a temperature sufficient to vaporize the liquid material in adjacent portions of the wick 28 and produce a vapor. The susceptor 14 may be located within the liquid reservoir component 70 proximate to and superposing at least a portion of an inlet portion 230 of the central air passage 20.

Still referring to FIG. 1, the susceptor 14 may be in the form of a thin disc or foil of electrically conductive and electrically resistive material. The material may be metallic and optionally magnetic. Examples of suitable electrically resistive/conductive materials which can be used to form the susceptor 14 include metals, alloys, and superalloys. For example, metals such as but not limited to nickel, cobalt, chromium, aluminium, titanium, zirconium, hafnium, niobium, molybdenum, tantalum, tungsten, tin, gallium, manganese, iron, platinum, osmium, iridium, ruthenium, rhodium, palladium, copper, and alloys thereof, can be used to form the susceptor 14. The susceptor 14 may include at least one material selected from the group consisting of stainless steel, copper alloys, nickel-chromium alloys, cobalt alloys, superalloys, and combinations thereof. In an alternate example embodiment, for example, the susceptor 14 can be formed of nickel aluminides, a material with a layer of alumina on the surface, iron aluminides, and other composite materials. The electrically resistive/conductive material may optionally be embedded in, encapsulated or coated with an insulating material or vice-versa, depending on the kinetics of energy transfer and the external physicochemical properties required.

In an example embodiment, the susceptor 14 is formed of nickel-chromium alloys or iron-chromium alloys. In another example embodiment, the susceptor 14 can be a ceramic composite susceptor having an electrically resistive/conductive layer on an outside surface thereof. In another example embodiment, the electrically resistive/conductive layer can be embedded in the ceramic susceptor.

In another example embodiment, the susceptor 14 may be constructed of an iron-aluminide (e.g., FeAl or $Fe_3Al$), such as those described in U.S. Pat. No. 5,595,706 to Sikka et al., or nickel aluminides (e.g., $Ni_3Al$).

When in the form of a metallic disc or foil, the susceptor 14 may be approximately 3 to 8 millimeters (mm) across and approximately the thinness of household aluminum foil.

Still referring to FIG. 1, the wick 28 may be constructed of a flexible, filamentary material. The wick 28 may include a plurality of filaments having sufficient capillarity via interstitial spaces between the filaments to draw liquid from the liquid reservoir 22; more the wick 28 may comprise a bundle of such glass, ceramic, or metal filaments and windings of filaments wound together into separate bundles or strands, wherein the wick 28 comprises a plurality of such bundles, such as three or more bundles or strands of wound fiberglass filaments.

The wick 28 can include filaments having a cross-section which is generally cross-shaped, clover-shaped, Y-shaped or in any other suitable shape.

The wick 28 may include any suitable material or combination of materials. Examples of suitable materials are glass filaments, fiberglass filaments, and ceramic, metal, or graphite based materials. Moreover, the wick 28 may have any suitable capillarity to accommodate vapor generating liquids having different liquid physical properties such as density, viscosity, surface tension and vapor pressure. The capillarity properties of the wick 28 and the properties of the liquid are selected such that the wick 28 is always wet in the area adjacent the susceptor 14 to avoid overheating of the susceptor 14 and/or the wick 28.

Referring now to FIGS. 1 and 5, a support 207 may support the susceptor 14 within the liquid reservoir component 70 in a fixed location relative to the wick 28 and/or the connector 205. In an example embodiment, the wick 28 includes a heatable wick portion (transverse middle portion) 228, which may extend across (is adjacent to) the upstream seal 15 and the upstream (inlet) portion 230 of the central air passage 20, and includes a first end portion 29 and also a second end portion 31, which extend longitudinally through the upstream seal 15 into the confines of the liquid reservoir 22 so as to be in contact with liquid in the liquid reservoir 22. Notches may be provided at locations along the perimeter of the upstream seal to accommodate placement of the end portions 29, 31 of the wick 28. It is contemplated that the wick 28 may include only one end portion 29 in communication with the reservoir, and that the placement and routing of the portions of the wick 28 may be other than as specifically described, so long as liquid is drawn from the liquid reservoir 22 into proximate relation with the susceptor 14, wherever located.

The susceptor 14 may be in thermal communication with the wick 28 and heats liquid in the wick 28 by thermal conduction. Alternatively, heat from the susceptor 14 may be transferred to a stream of incoming ambient air that is drawn through the e-vaping device 60 during use, which in turn heats the liquid material by convection.

The liquid reservoir component 70 (cartridge) further includes a mouth end insert 8 having two or more, off-axis, diverging outlets 24, e.g., four of such outlets 24. Alternatively, the mouth end insert 8 can have a single outlet 24. The mouth end insert 8 is in fluid communication with the central air passage 20 defined by the interior of inner tube 62.

Still referring to FIGS. 1 and 5, locating the susceptor 14 adjacent the inlet portion 230 of the central channel 20 promotes fuller vapor formation by providing a generally straight flow path from the location of the susceptor 14 (where vapor is first formed) to the interior of the mouth end insert 8. Such an arrangement avoids abrupt changes in direction of flow and avoids associated losses due to impaction and other effects which would otherwise impede vapor development and production. Also the central air passage 20 minimizes contact and thermal transfer between the vapor and the walls of the liquid reservoir 22.

The liquid material in the liquid reservoir 22 may have a boiling point suitable for use in the e-vaping device 60. If the boiling point is too high, the susceptor 14 will not be able to vaporize liquid off the wick 28. However, if the boiling point is too low, the liquid may vaporize prematurely without the susceptor 14 being activated.

The liquid material may include a tobacco-containing material including volatile tobacco flavor compounds which are released from the liquid upon heating. The liquid may also be a tobacco flavor containing material or a nicotine-containing material. Alternatively, or in addition, the liquid may include a non-tobacco material. For example, the liquid may include water, solvents, ethanol, plant extracts, acids, caffeine, and natural or artificial flavors. The liquid may further include a vapor former. Examples of suitable vapor formers are glycerine and propylene glycol.

One advantage of the wick arrangement is that the liquid material in the liquid reservoir 22 is protected from oxygen (because oxygen cannot generally enter the liquid storage portion via the wick) so that the risk of degradation of the liquid material is significantly reduced. Moreover, by using an opaque outer casing 6, the liquid reservoir 22 is protected from light so that the risk of degradation of the liquid material is significantly reduced. Thus, a high level of shelf-life and cleanliness can be maintained.

Referring now to FIG. 3, in an example embodiment, the susceptor 14 comprises a wire coil which at least partially surrounds the wick 28. The wire coil may extend fully or partially around the circumference of the wick 28 with or without spacing between the turns of the coil. In another example embodiment, the susceptor coil is located adjacent but is not wound about the wick 28. Moreover, a downstream gasket 10 is fitted into a downstream end portion of the inner tube 62.

The Battery Section

Referring now to FIG. 1 (and FIG. 5) the battery section 72 comprises an outer casing 6 extending in a longitudinal direction and includes a power source or battery 1 in electrical communication with an induction source 35 through control circuitry 16.

The battery or power source 1 can be a Lithium-ion battery or one of its variants, for example a Lithium-ion polymer battery. Alternatively, the battery may be a Nickel-metal hydride battery, a Nickel cadmium battery, a Lithium-manganese battery, a Lithium-cobalt battery or a fuel cell. In that case, the e-vaping device 60 may be usable by an adult vaper until the energy in the power source is depleted. Alternatively, the power source 1 may be rechargeable and include circuitry allowing the battery to be chargeable by an external charging device. In that case, the circuitry, when charged, may provide power for a pre-determined number of puffs, after which the circuitry must be re-connected to an external charging device.

Figure 2:
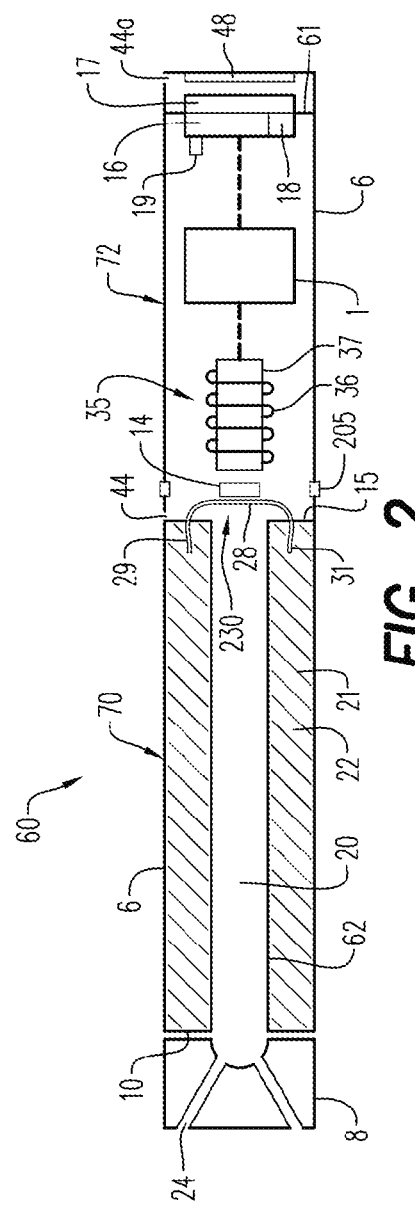
FIG. 2 is a cross-sectional view of an e-vaping device according to an example embodiment disclosed herein.

The control circuitry 16 may include an oscillator 18 which is operable to oscillate the power supplied to the induction source 35 such that the latter generates an oscillating inductive field in a desired direction and time period such the induction source 35 may be capable of causing the susceptor 14 to heat, to a predetermined and/or desired temperature and for a predetermined and/or desired time period. The control circuitry 16 may also include a voltage regulator 19 such that the voltage across the induction source 35 is controlled. The induction source 35 may be powered by the power source 1 via the oscillator 18 at a frequency of about 100 kHz to 1 MHz wherein the frequency is selected based upon the skin depth of the susceptor 14, the axial spacing between the susceptor 14 and the induction source 35, and parameters of the induction source 35. In the case of a primary induction coil 36 as shown in FIG. 2, those parameters include the spacing between turns and the number of turns. The frequency may also depend upon the characteristics of a ferrite core 37 about which the induction coil 36 is wound. Details of an induction source and susceptor can be found in U.S. Pat. No. 5,613,505, which is incorporated herein by reference in its entirety.

In an example embodiment, for example as illustrated in FIG. 2, the axis of symmetry of the primary induction coil 36 and ferrite core 37 extends in the longitudinal direction of the outer casing 6, and in an alternate example embodiment, for example as illustrated in FIG. 4, the axis of symmetry of the induction coil 36 and ferrite core are oriented transversely.

Referring now to FIGS. 1 and 5, the control circuitry 16 may communicate responsively with a puff sensor (pressure sensor) 17 that may be located at a distal end portion of the battery section 72. The puff sensor 17 is operable to generate a signal responsive to air being drawn from the e-vaping device 60 through the mouth end insert 8. In response to the signal from the puff sensor 17, the control circuitry 16 communicates an oscillating power cycle to the induction source 35. The pressure drop of a draw (or puff) upon the mouth end insert 8 of liquid reservoir component 70 is communicated to the puff sensor 17 through openings 44b and 44c (FIGS. 5 and 6) in components 70 and 72, respectively, adjacent the connector 205, and via spaces provided between the battery 1 and adjacent portions of the casing 6. The puff sensor 17 may be operable to generate more than one signal, such as a range of signals responsive to the magnitude of a puff or draw upon the e-vaping device 60 so that the control circuitry 16 can discriminate between the signals to adjust the frequency, magnitude, and/or length of time of the immediate power cycle in response to the signal it receives from the puff sensor.

A partition 61 may be provided at or upstream of the puff sensor 17 to isolate a pressure relief inlet 44a which is located at the distal end of the battery section 7. The pressure relief inlet 44a serves to relieve pressure on its side of the puff sensor 17, which would otherwise interfere with facile operation of the puff sensor 17. In an example embodiment, the puff sensor 17 and control circuitry 16 can be a single chip such as a MP909 chip from ChipTech. The MP909 chip is an integrated circuit with resistors and timing circuits, inputs and outputs which can function to cause switching (i.e., supply power from the power source to the induction source based on the puff sensor signal, and to cause the LED to blink when power is low, and other functionalities.).

Referring to FIGS. 3, 5, and 6, the power source 1 can include a battery arranged in the e-vaping device 60 wherein a battery anode connector can connect the anode of the battery with one pole of the induction source 35 and a battery cathode connector can connect the cathode of the battery with another pole of the induction source 35 such that an inductive field can be generated. The susceptor 14 is heated when the induction source 35 generates an inductive field wherein the susceptor 14 is disposed within the inductive field.

The control circuitry 16 may be configured to provide a power cycle whose elements achieve optimal ramp-up in temperature of the susceptor 14 and maintenance of an operating temperature for a predetermined and/or desired period of time. For example, the power cycle may be divided into two (or more) phases each having a respective time period of T1 and T2. In the first phase (T1), a higher frequency and/or magnitude of oscillation may be employed so as to induce rapid heating in the susceptor 14. In the second phase (T2), the control circuitry 16 can provide a power cycle with a more moderate frequency and/or a more moderate magnitude of oscillation so as to achieve steady heating effect throughout the second phase (T2). Through testing, analytics and/or modeling, a desired power cycle may be established. The power cycles could include a plurality of phases wherein only the amplitude or only the frequency is varied and may include phases wherein there is no power and/or oscillation being directed to the induction source 35.

The control circuitry 16 can control the induction source 35 such that an alternating inductive field is generated, or in an alternate example embodiment, the control circuitry 16 can pulse the induction source 35 between an on and off state such that the generated inductive field may heat the susceptor 14. The pulsing can control the susceptor 14 temperature and vapor production.

The control circuitry 16 may be configured also to adjust frequency, magnitude and/or time period responsive to readings of battery voltage so that consistent performance is maintained as the voltage level of the battery 1 declines during use.

The puff sensor 17 may be operable to generate more than one signal, such as a range of signals responsive to the magnitude of a puff or draw upon the mouth end insert 8 so that the control circuit 16 can discriminate between the signals to adjust the frequency, magnitude, and/or time of the immediate power cycle in response to the signal it receives from the puff sensor 17. For instance a heavy draw might generate a first signal from the puff sensor 17, which in turn would cause the control circuitry to extend the time of the immediate power cycle responsively or make some other adjustment in the power cycle to provide a greater production of vapor.

When activated, the susceptor 14 may heat a portion of the wick 28 surrounded by the susceptor for less than about 10 seconds, more preferably less than about 7 seconds. Thus, the power cycle (or maximum puff length) can range in period from about 2 seconds to about 10 seconds (e.g., about 3 seconds to about 9 seconds, about 4 seconds to about 8 seconds or about 5 seconds to about 7 seconds).

Alternatively, the control circuitry 16 may include a manually operable switch for an adult vaper to initiate a puff. The time-period and characteristics of the electric current supply to the induction source 35 may be pre-set depending on the amount of liquid desired to be vaporized. The control circuitry 16 may be pre-programmed or programmable for this purpose. Alternatively, the circuitry 16 may supply power to the induction source 35 as long as the puff sensor 17 detects a pressure drop.

The control circuitry 16 can also include a LED 48 operable to glow when the susceptor 14 is activated. The LED 48 may be at an upstream (distal) end of the e-vaping device 60 so that the LED 48 mimics the appearance of a burning coal during a puff. The LED 48 can be arranged to be visible to the adult vaper. In addition, the LED 48 can be utilized for vaping system diagnostics. The LED 48 can also be configured such that the adult vaper can activate and/or deactivate the LED 48 for privacy, such that the LED 48 would not activate during vaping if desired.

Referring now to FIG. 6, upon closure of the connector 205, the induction source 35 is positioned a predetermined and/or desired axial distance from the susceptor 14. The distance may be less than 2 mm, and more preferably less than 1 mm.

Reusable Power Supply Component and Replaceable Liquid Reservoir Component

Figure 13:
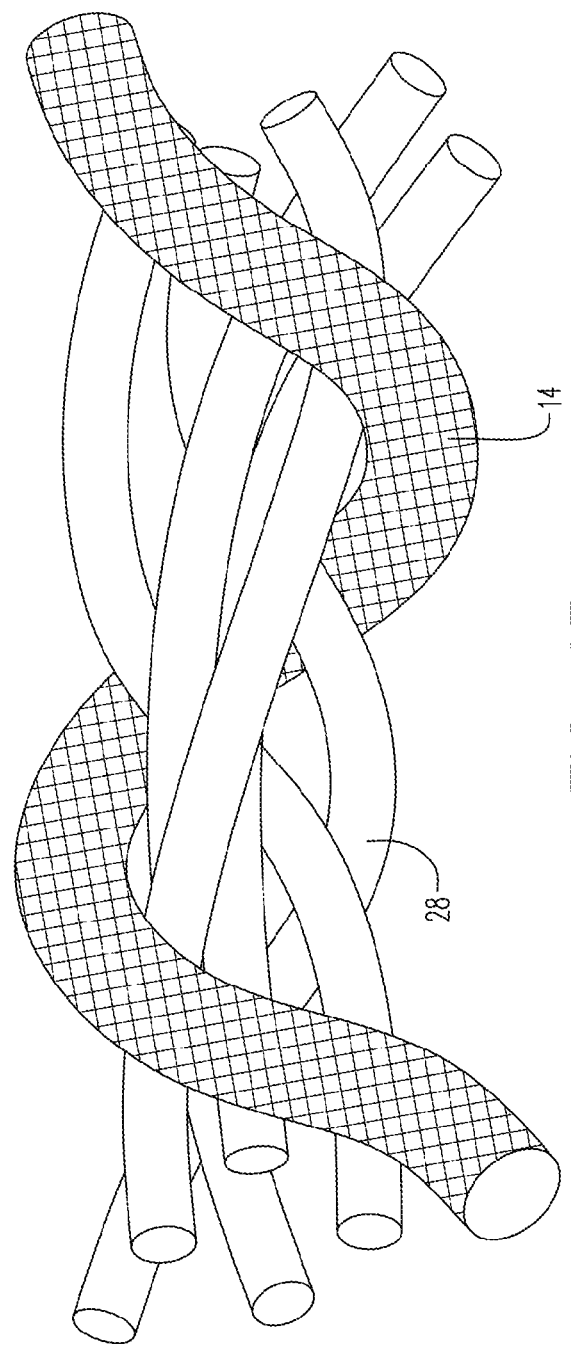
FIG. 13 is a detail view of yet another example embodiment of an integrated susceptor and wick element, operable in a liquid reservoir component such as shown in FIGS. 11A and 11B.

Referring now to FIGS. 3 and 13, another example embodiment has components and functionalities like those described with respect to the example embodiments shown and described with reference to FIGS. 1 and 5, except that the susceptor 14 can be in the form of a wire coil (or wire cage) 14 of conductive/resistive material disposed about the filaments of a wick 28 so as to establish an integrated wick/susceptor element 28/14. Optionally, the wire material may be magnetic.

Figure 12:
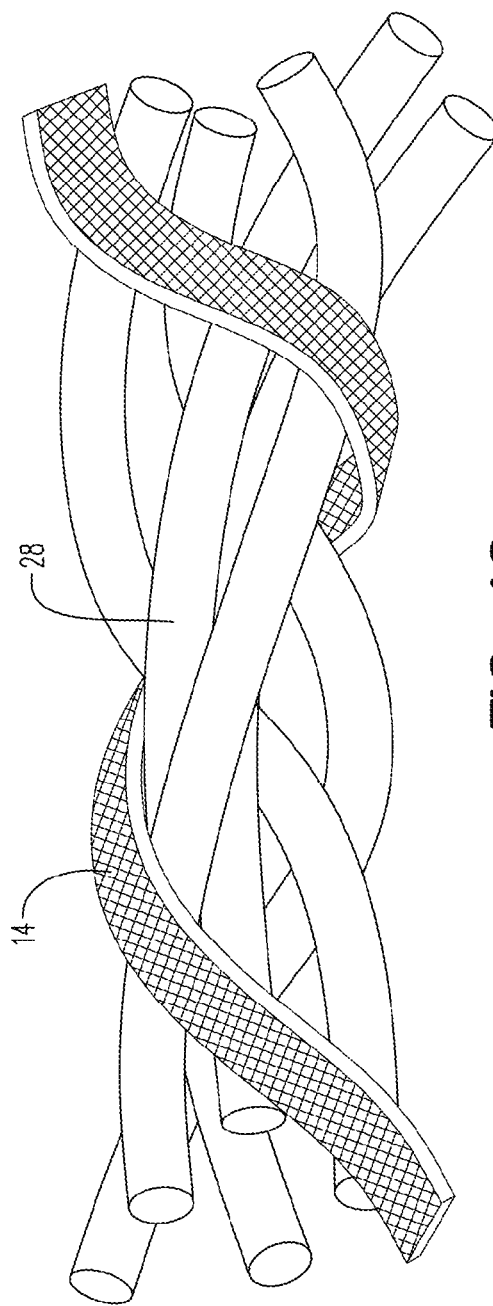
FIG. 12 is a detail view of another example embodiment of an integrated susceptor and wick element, operable in a liquid reservoir component such as shown in FIGS. 11A and 11B.

There are provided further example embodiments which include an integrated wick/susceptor element 28/14. Referring now generally to FIGS. 11A and 11B and specifically to FIG. 11C, the susceptor 14 may comprise one or more inductively heatable, wire filaments which are electrically resistive/conductive and are intertwined (integrated with) with filaments of the wick 28 to form an integrated wick/susceptor element 28/14. Referring now also to FIG. 12, alternatively or in addition to, the susceptor 14 may be wound about the wick 28 wherein the susceptor 14 is an inductively heatable ribbon of electrically resistive/conductive mesh material. It is envisioned that the mesh material may be intertwined among the wick filaments of the wick/susceptor 28/14. Referring now to FIG. 14, another example embodiment may include inductively heatable, electrically resistive/conductive flakes 14 of thin foil or metallic material which are disposed along a heatable portion of the wick 28 so as to establish another form of an integrated wick/susceptor assembly 28/14. The flakes 14 may have any shape such as a rectangular, triangular, or oblong shape or a combination thereof wherein the flakes 14 may provide a more rapid response to inductive heating and may exhibit a more efficient transfer of heat to liquid adjacent the heated flakes 14, because of their small size (less than 1 mm in width, more preferably, less than about 0.5 mm in width).

Referring specifically to FIGS. 8A and 8B, in an alternate example embodiment, the integrated wick/susceptor element 28/14 can be formed from a conductive mesh which can wick liquid material from the liquid reservoir 22, wherein a heatable portion 801 of the conductive mesh may be disposed adjacent the inlet portion 230 of the central air passage 20. The mesh, wick/susceptor element 28/14 may include two or more layers of woven stainless steel threads or mesh, the properties of the mesh material and the number of layers being selected so as to achieve sufficient capillarity to have the capacity to draw liquid toward the heatable portion 801 of the integrated wick/susceptor element 28/14. It is contemplated that the integrated wick/susceptor element 28/14 may have its heatable (central) portion 801 differ in density, fiber length, chemistry, number of layers, width and in other ways from end portion(s) of the element 28/14 which does the wicking, such that the central portion is configured to optimize inductive heating and/or thermal transfer and the end portion(s) of the element 28/14 is/are optimized for wicking.

Further Example Embodiments

In a further example embodiment of an e-vaping device 60, referring now to FIGS. 5 and 6, the liquid reservoir component 70 thereof can include the air inlet 44, the outlet located 24 downstream of the air inlet, and the straight internal passageway 20 having the inlet end portion 230 wherein the straight internal passageway 20 communicates with the air inlet 44 and the air outlet 24 through the inlet end portion 230. The liquid reservoir component 70 includes the liquid reservoir 22, and the wick 28 having the heatable wick portion 228, the first end portion 29, and the second end portion 31. The heatable wick portion 228 may be in proximity of and disposed across at least a portion of the inlet end portion 230 of the straight internal passageway 20. The first and second end portions 29, 31 may be arranged to draw liquid from the liquid reservoir 22 to the heatable wick portion 228. A susceptor 14 may be in proximal relation to the heatable wick portion 228 wherein the susceptor 14 is adapted to produce heat in the presence of an activating, oscillating electromagnetic field sufficient to volatilize liquid off the heatable wick portion 228 wherein the activating, oscillating electromagnetic field is produced by an electromagnetic field source 72 (e.g. a power supply component) separate of the liquid reservoir component 70. The proximity of the heated wick portion to the inlet end portion of the straight internal passageway 20 may be sufficient for the volatilized liquid to be drawn directly into the inlet end portion 230 of the straight internal passageway 20 whereupon a vapor is formed with minimal degradation.

The liquid reservoir component 70 may include an outer casing 60 having an outlet end portion and an opposite end portion wherein a connector 205 may be at the opposite end portion. The connector 205, upon closure, is adapted to releasably couple the liquid reservoir component 70 with the separate electromagnetic energy source 72. A support 207 may be arranged to maintain the susceptor 14 in a fixed relation to the opposite end portion of the outer casing 6 such that upon closure of the connector 205, the susceptor 14 is axially spaced from the separate electromagnetic energy source 72 by a predetermined and/or desired distance.

Referring now to specifically FIG. 5, the battery section 72 may include a seal 233 adjacent the coupling 205 so as to protect the electronic contents of the battery section 72 from external elements.

In a further example embodiment, referring now to FIG. 15, in an example embodiment of an e-vaping device 60, the control circuitry 16 is separate from the puff sensor 17 in the power supply component 72 and the control circuitry 16 is disposed downstream of the power supply 1. The puff sensor 17 may be at the distal end of the power supply component 72 wherein a partition 61 may isolate a downstream side the puff sensor 17 from the remainder of the power supply component 72.

Referring to FIGS. 7A and 7B, in an example embodiment, the liquid reservoir component 70 can include a filamentary wick 28 which superposes the inlet portion 230 of the central air passage 20, wherein a susceptor 14 comprises a planar screen of electrically conductive/resistive material and is optionally air permeable. In this example embodiment and others, the susceptor 14 is supported on an internal annular flange 41 of the liquid reservoir component 70. The susceptor 14 can be affixed to the flange 41 by any suitable means such as by a snap-fit or by a heat resistant adhesive. In this example embodiment and others, the air inlets 744a, 744b may comprise two or more convergently directed channels (convergent toward the mouth end insert of the e-vaping device 60) and each may include a beveled rim at the outer surface of the casing 6 so as to minimize the generation of a whistling noise during a draw on the e-vaping device 60. The air inlets 744a, 744b may release air into the liquid reservoir component 70 at a location upstream of the flange 41. In this example embodiment the susceptor 14 may comprise a foil disc or a perforated foil. It is contemplated that air inlets 744a, 744b may be configured to release air upstream of the flange 41 instead.

Referring to FIGS. 9A and 9B, in an example embodiment, an air permeable susceptor 14 comprises a screen disc or perforated foil disc positioned across the central air passage 20, adjacent to and downstream of the filamentary wick 28. Optionally, the susceptor 14 is supported from (or affixed to) the seal 15, with a thermally insulatory gasket 33 being interposed between the seal 15 and the susceptor 14 to protect the seal 15 from thermal degradation.

Referring now to FIGS. 10A and 10B, in an example embodiment, the upstream seal 15 at the inlet portion 230 of the central channel 20 comprises a wick structure including a first, liquid transmissive, porous toroidal layer 28a which covers the upstream inlet (end) portion 230 of the liquid reservoir 22 such that it surrounds, but may not occlude, the central air passage 20, and an insulatory second layer 28b in the form of a disc which covers the first layer 28a and may extend across the central air passage 20. The first layer 28a may be constructed from a sintered polymer, such as those employed as wicks in ink markers, or from a sintered, porous metal. The second, upstream layer 28b may include a loose weave or mat of fiberglass having a greater degree of capillarity and air permeability than the first layer 28a. The wick layers 28a, 28b cooperate with a susceptor 14 positioned nearby as previously taught herein. The first layer 28a may be a disk of perforated material, wherein the first layer 28a can draw liquid from the liquid reservoir 22, whereupon the liquid can be transferred from the first layer 28a to the second layer 28b. The second layer 28b may be a fiberglass cover, tightly held against the first layer 28a, wherein the fiberglass has a loose weave such that it is air permeable. Alternatively, the second layer 28b can be an air permeable material which has the capacity to wick liquid such that the liquid disposed in thermal communication with the susceptor 14 can be vaporized (volatilized). The air permeable material forming the second layer 28b may withstand temperatures of up to 400° C. In this example embodiment the susceptor 14 may comprise a screen disc or a foil disc held in proximate relation to the second wick layer 28a.

Referring to FIG. 16, in an example embodiment, the susceptor 14 and the wick 28 are integral with one another and form a wick/susceptor 28/14. The wick/susceptor 28/14 may be an electrically resistive/conductive mesh screen which can wick liquid from the liquid reservoir 22 to a central region thereof. When the liquid reservoir component 70 is connected via the connector 205 to the power supply component 72 the wick/susceptor 28/14 is axially spaced a predetermined and/or desired distance from the induction source 35. When the power source 1 is powered, the induction source 35 which is in communication with the power source 1 and the control circuitry 16, which includes the voltage regulator 19 and oscillator 18, forms a resonance circuit contained wholly in the power supply component 72. In this manner, the induction source 35 is operable to generate an inductive field to heat the wick/susceptor 28/14 and volatize the liquid at the central region of the wick/susceptor 28/14. Thus, no electrical connections between the liquid reservoir component 70 and the power supply component 72 are needed.

Referring to FIG. 17, in an example embodiment, a disk-shaped wick 28 extends across the central air passage 20 and a thermally transmissive element 73 thermally communicates heat from a heater 27 to the wick 28. The heater 27, such as a ceramic resistive heater or an inductively heated susceptor, contacts the thermal element 73 such that the heater 27 when powered by the power source 1 through the control circuitry 16 is operable to transfer heat through the thermal element 73 and heat liquid drawn by the wick 28 to volatilize the liquid and form a vapor. The thermally transmissive element 73 may be in the form of a rod or the like (so that air may be drawn around it) and is a part of the liquid reservoir component 70, whereby air may be drawn through the air inlets 44 and past the thermally transmissive element 73 and into the central air channel 20. The thermally transmissive element 73 also serves to maintain spacing between the heater 27 and the wick 28 so as to prolong cleanliness of the heater 27.

Referring to FIG. 18A, in a further example embodiment, the induction source 35 of the power supply component 72 is configured to extend into a region (confines) of the liquid reservoir component 70 such that when the power supply component 72 is connected to the liquid reservoir component 70 the induction source 35 is at least partially surrounded by the susceptor 14. The susceptor, represented in FIG. 18A by feature A, may be formed of an electrically conductive/resistive element 14' (See FIG. 18B) that has the capacity to wick liquid material from the liquid reservoir 22, or the susceptor is coupled with a wicking layer (28) so as to form an integrated wick/susceptor 28/14 (See FIG. 18C) which may be in communication with a portion of the liquid storage medium 21 in the liquid reservoir 22, in a region of the liquid reservoir 22 adjacent the inlet portion 230 of the central channel 20. By such an arrangement, the wick/susceptor 28/14 wicks the liquid material from the liquid storage medium 21. A portion of the liquid storage medium 21 may surround the susceptor 14, or alternatively the wick/susceptor 28/14.

Still referring to FIG. 18A, in an alternative example embodiment, the liquid storage medium 21 is configured to contact a susceptor, represented by feature A, which is an electrically resistive/conductive cylinder wherein when the susceptor is heated, it directly heats liquid material in the liquid storage medium 21 such that the liquid may be volatized. The volatilized liquid may be drawn into the central air passage 20 through gaps or holes 319 provided in the susceptor (see FIG. 18C). The induction source 35 may include the inductive coil 36 wound about the cylindrical core 37 comprising a ferrite material. The inductive coil 36 and the cylindrical core 37 may extend in the longitudinal direction of the outer casing 6. The inductive coil 36 may be a helix wound about the cylindrical core 37, however in an alternate example embodiment, the inductive coil 36 can be a planar coil wherein the planar coil may surround the cylindrical core 37.

Referring now to FIGS. 16-18A, the power supply component 72 may be connected to the liquid reservoir component 70 at the connector 205 which may be a threaded connection. Air inlets 44 may be included in the liquid reservoir component 70 wherein the air inlets 44 are adjacent the threaded connection. Each air inlet 44 may include a beveled entrance and an angled passageway. In an example embodiment, the e-vaping device 60 includes a pair of air inlets 44. Each of the air inlets 44 is angled toward the mouth end insert 8 of the e-vaping device 60 at an angle in the range of about 35° to about 55° with respect to the longitudinal axis of the article 60, more preferably at about 40° to about 50°, most preferably about 45°. Such arrangement minimizes (abates) "whistling" noise during a draw on the e-vaping device 60.

Figure 19:
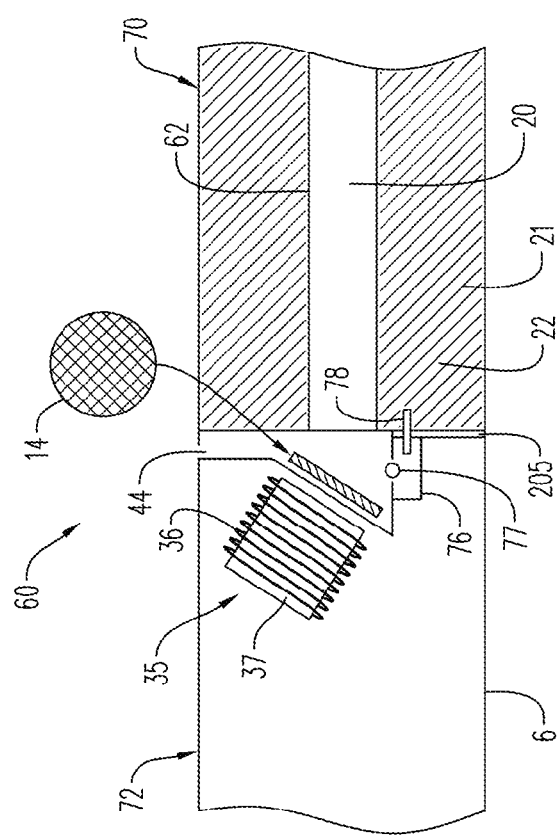
FIG. 19 is a cross-sectional view of an e-vaping device according to an example embodiment disclosed herein.

Referring now to FIG. 19 in an additional example embodiment, the battery section 72 can include a piezoelectric element 76 which includes a capillary element (or needle) 78 which extends into the liquid reservoir 22 of the liquid reservoir component 70 upon closure of the connector 205 between the cartridge component 70 and battery section 72. The piezoelectric element 76 is operable responsively to a puff sensor 17 (as taught above). The piezoelectric element 76 delivers liquid droplets from a discharge port 77 to an adjacent susceptor 14 when an adult vaper draws on the e-vaping device 60. An induction source 35 is also activated responsively to a puff sensor 17 (as taught above). Thereupon, the susceptor 14 vaporizes the liquid droplets to form a vapor which is drawn through the central air passage 20. The output of the piezoelectric element 76 (liquid droplets) is directed transversely onto a susceptor 14 whose operative surface is set at an angle relative to the longitudinal axis of the e-vaping device 60 so as to present itself to the stream of droplets, produced by the piezoelectric element 76. It is envisioned that the angular relation could be reversed or that both components are set at an angle. It is contemplated that a wick 28 may be positioned adjacent the susceptor so that the wick 28 receives the output of the piezoelectric element 76 instead of the susceptor 14. Such a wick 28 may be made part of the cartridge section 70, so as to be replaced with every change of the cartridge section 70.

Figure 21:
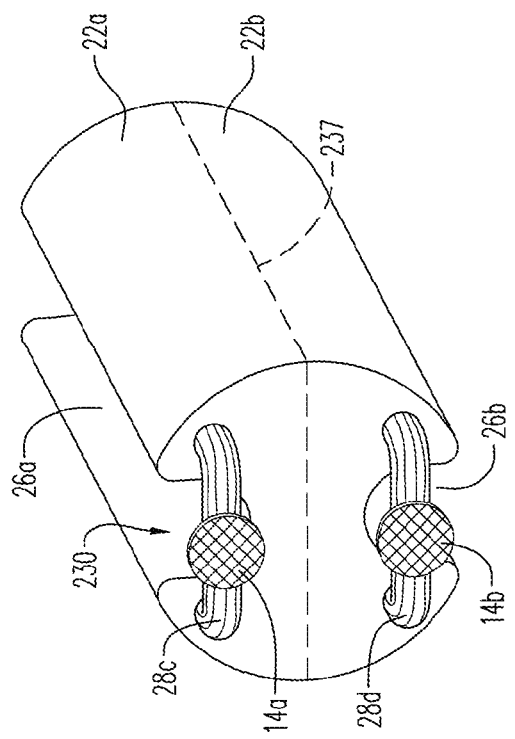
FIG. 21 is a perspective view of a liquid reservoir component of an e-vaping device according to an example embodiment disclosed herein.
Figure 20:
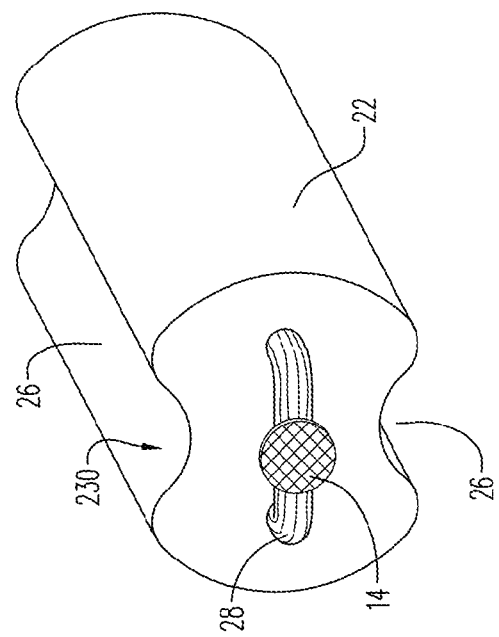
FIG. 20 is a perspective view of a liquid reservoir component of an e-vaping device according to an example embodiment disclosed herein.

Referring now to FIGS. 20 and 21, in an example embodiment, the liquid reservoir 22 can be a self-supporting element and shaped to include a longitudinal recess along a wall of the liquid reservoir 22 such that an air channel 26 or multiple air channels 26 are defined between the reservoir wall and adjacent portions of the casing 6. An arrangement of a wick 28 and susceptor 14 extends across and is adjacent to an inlet (end) portion 230 of each channel 26 in accordance the teachings provided above. It is also contemplated that the liquid reservoir 22 could be separated by an internal partition 237 (represented by dashed lines in FIG. 21) into a first liquid reservoir 22a, and a second liquid reservoir 22b, wherein each liquid reservoir 22a, 22b, includes a respective channel 26a, 26b, and further each liquid reservoir includes a respective wick 28c, 28d, and respective susceptor 14a, 14b operable to heat each respective wick 28c, 28d (see FIG. 21). In this example embodiment, each liquid reservoir 22a, 22b, can include a different liquid material, such that vapors formed from the liquid material may mix in the e-vaping device 60, or alternatively, the vapors formed by the different liquid materials may mix in an adult vaper's mouth.

In some example embodiments, the e-vaping device 60 can be about 80 mm to about 110 mm long, preferably about 80 mm to about 100 mm long and about 10 mm or less in diameter. For example, in an example embodiment, the e-vaping device is about 84 mm long and has a diameter of about 7.8 mm. In an alternate example embodiment, the e-vaping device 60 may be larger. It may also be in a form other than cylindrical, such as one having a square cross-section, or a triangular or rectangular cross-section.

The outer casing 6 and/or the inner tube 62 may be formed of any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK), ceramic, and polyethylene. The material may be light and non-brittle.

Having a separate liquid reservoir component 70 and power supply component 72 allows the susceptor 14, wick 28, and liquid reservoir 22, which are in contact with the liquid material to be disposed of when the liquid reservoir component 70 is depleted, and allows the power supply component 72 to be reusable. Thus, there will be no cross-contamination between different mouth end inserts 8, for example, when using different liquid materials. Also, if the liquid reservoir component 70 is replaced at suitable intervals, there is little chance of the susceptor 14 and/or wick 28 becoming clogged with liquid material. Further, locating all electrical connections in the power supply component 72 wherein there are no wires connecting the power supply component 72 to the liquid reservoir component 70 simplifies assembly and reduces the cost of manufacture of the e-vaping device 60.

The teachings herein describe example embodiments of e-vaping devices 60 comprising a reservoir component 70 and a battery component 72, however, it is envisioned that the e-vaping device 60 may be constructed as a single-piece article 60, lacking a connector 205.

Whereas the example embodiments are described as being cylindrical, other suitable forms include right angular, triangular, oval, oblong, or other cross-sections.

When the word "about" is used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages.

Moreover, when the words "generally" and "substantially" are used in connection with geometric shapes, it is intended that precision of the geometric shape is not required but that latitude for the shape is within the scope of the disclosure.

It will now be apparent that a new, improved, and non-obvious e-vaping device has been described in this specification with sufficient particularity as to be understood by one of ordinary skill in the art. Moreover, it will be apparent to those skilled in the art that modifications, variations, substitutions, and equivalents exist for features of the e-vaping device which do not materially depart from the spirit and scope of the example embodiments disclosed herein. Accordingly, it is expressly intended that all such modifications, variations, substitutions, and equivalents which fall within the spirit and scope of the invention as defined by the appended claims shall be embraced by the appended claims.

We claim:

1. An electronic vaping (e-vaping) device comprising:
a pre-vapor formulation storage element connectable to a power supply, the pre-vapor formulation storage element configured to contain a pre-vapor formulation material and including a fibrous material, the pre-vapor formulation material being absorbed in the fibrous material, the pre-vapor formulation storage element further including,
an outer casing extending in a longitudinal direction,
an air inlet,
a vapor outlet,
an inner tube within the outer casing defining a central air passage communicating with the air inlet and the vapor outlet, and
a susceptor located adjacent the central air passage, the susceptor being operable to heat the pre-vapor formulation material to a temperature to vaporize the pre-vapor formulation material; and
the power supply including,
an outer casing extending in a longitudinal direction including a power source in electrical communication with an induction source, the induction source being axially spaced from the susceptor by a distance if the power supply is attached to the pre-vapor formulation storage element such that the induction source is operable to generate an inductive field to heat the susceptor if powered by the power source such that the susceptor heats the pre-vapor formulation material to a temperature to vaporize the pre-vapor formulation material.

2. The e-vaping device of claim 1, wherein the induction source includes an inductive coil at an end thereof proximate to the susceptor of the pre-vapor formulation storage element, and the inductive coil is configured to generate the inductive field to heat the susceptor.

3. The e-vaping device of claim 2, wherein the inductive coil comprises a helix extending in the longitudinal direction of the outer casing.

4. The e-vaping device of claim 2, wherein the inductive coil comprises a planar coil.

5. The e-vaping device of claim 2, wherein the inductive coil comprises a helix extending in a transverse direction to the longitudinal direction of the outer casing.

6. The e-vaping device of claim 2, wherein the induction source further includes a cylindrical core comprising a ferrite material, the inductive coil is wound about the cylindrical core and the cylindrical core extends in the longitudinal direction of the outer casing or in a transverse direction to the longitudinal direction of the outer casing.

7. The e-vaping device of claim 1, wherein the susceptor comprises one of stainless steel, copper, copper alloys, ceramic material coated with film resistive material, nickel chromium alloys, or a sub-combination thereof or a combination thereof.

8. The e-vaping device of claim 1, wherein the pre-vapor formulation storage element further includes a mouth end insert and the mouth end insert is in communication with the air inlet.

9. The e-vaping device of claim 1, wherein the susceptor is axially spaced from a proximate end of the induction source by about 0.01 to 2 mm if the pre-vapor formulation storage element is connected to the power supply.

10. The e-vaping device of claim 1, wherein
a portion of the power supply is in the pre-vapor formulation storage element if the power supply and the pre-vapor formulation storage element are connected and the susceptor is axially spaced from a proximate end of the induction source, or
a portion of the pre-vapor formulation storage element is in the power supply if the power supply and the pre-vapor formulation storage element are connected and the susceptor is axially spaced from a proximate end of the induction source.

11. The e-vaping device of claim 1, wherein the power supply further comprises control circuitry including a puff sensor, and the puff sensor is configured to sense air flow and initiate generation of the inductive field from the induction source in electrical communication with the power source.

12. The e-vaping device of claim 11, wherein the control circuitry is configured to control a variable power cycle from the power source to the induction source as a function of an output signal of the puff sensor.

13. The e-vaping device of claim 1, wherein one of
the pre-vapor formulation storage element is connected to the power supply with a mechanical or magnetic connection;
the pre-vapor formulation storage element is a disposable downstream section and the power supply is a reusable upstream section; or
the pre-vapor formulation storage element is connected to the power supply with a mechanical or magnetic connection and the pre-vapor formulation storage element is a disposable downstream section and the power supply is a reusable upstream section.

14. The e-vaping device of claim 1, wherein the susceptor is made of a magnetic material.

15. An electronic article comprising the e-vaping device of claim 1, the electronic article having a uniform diameter of about 10 mm or less, wherein the power supply further includes, a puff sensor configured to sense air flow and initiate generation of the inductive field from the induction source in electrical communication with the power source.

16. The e-vaping device of claim 1, wherein the susceptor is formed in a disk-like shape.

17. The e-vaping device of claim 1, wherein the induction source includes an inductive coil wound about a cylindrical core, the cylindrical core including a ferrite material.

18. The electronic article of claim 15, wherein the susceptor is formed in a disk-like shape.

19. The electronic article of claim 15, wherein the induction source includes an inductive coil wound about a cylindrical core, the cylindrical core including a ferrite material.

* * * * *